US007629355B2

(12) United States Patent
Lawson

(10) Patent No.: US 7,629,355 B2
(45) Date of Patent: Dec. 8, 2009

(54) TREATMENT OF CHEMICAL DEPENDENCY WITH SUBSTANTIALLY NONADDICTING NORMORPHINE AND NORCODEINE DERIVATIVES

(76) Inventor: John A. Lawson, 1465 E. 800 N., Logan, UT (US) 84321

(*) Notice: Subject to any disclaimer, the term of this patent is extended or adjusted under 35 U.S.C. 154(b) by 974 days.

(21) Appl. No.: 10/967,098

(22) Filed: Oct. 14, 2004

(65) Prior Publication Data

US 2005/0113401 A1 May 26, 2005

Related U.S. Application Data

(60) Provisional application No. 60/511,279, filed on Oct. 14, 2003.

(51) Int. Cl.
    *A61K 31/44* (2006.01)
(52) U.S. Cl. ..................... 514/282
(58) Field of Classification Search ................. 514/282
    See application file for complete search history.

(56) References Cited

U.S. PATENT DOCUMENTS

| 4,218,454 A * | 8/1980 | DeGraw et al. ............ 514/282 |
| 4,749,706 A * | 6/1988 | Lawson et al. ............ 514/282 |
| 4,948,803 A | 8/1990 | Tyers |
| 5,366,979 A | 11/1994 | Lawson |

OTHER PUBLICATIONS

Bickel et al. (1988), "A Clinical Trial of Buprenorphine: Comparison with Methadone in the Detoxification of Heroin Addicts," *Clin. Pharmacol. Ther.* 43(1):72-78.
Branch et al. (1992), "Quantitation of Preproenkephalin mRNA Levels in Brain Regions from Male Fischer Rats Following Chronic Cocaine Treatment Using a Recently Developed Solution Hybridization Assay," *Molecular Brain Research* 14:231-238.
Crawford et al. (1995), "The Effects of the Kappa Agonist U-50,488 on Cocaine-Induced Conditioned and Unconditioned Behaviors and Fos Immunoreactivity," *Psychopharmacology* 120:392-399.
Daunais et al. (1993), "Cocaine Self-Administration Increases Preprodynorphin, but Not c-Fos, mRNA in Rat Striatum," *NeuroReport* 4(5):543-546.
Johnson et al. (1992), "A Controlled Trial of Buprenorphine Treatment for Opioid Dependence," *JAMA* 267(20):2750-2755.
Kuzmin et al. (2000), "Influence of Buprenorphine, Butorphanol and Nalbuphine on the Initiation of Intravenous Cocaine Self-Administration in Drug Naïve Mice," *European Neuropsychopharmacology* 10:447-454.
Mello et al. (1982), "Buprenorphine Effects on Human Heroin Self-Administration: An Operant Analysis," *The Journal of Pharmacology and Experimental Therapeutics* 223(1):30-39.
Mello et al. (1993), "Buprenorphine Treatment of Opiate and Cocaine Abuse: Clinical and Preclinical Studies," *Harvard Review Psychiatry* 1(3):168-183.
Mello et al. (1998), "Effects of *Kappa* Opioid Agonists on Cocaine- and Food-Maintained Responding by Rhesus Monkeys," *The Journal of Pharmacology and Experimental Therapeutics* 286(2):812-824.
Negus et al. (1997), "Effects of *Kappa* Opioids on Cocaine Self-Administration by Rhesus Monkeys," *The Journal of Pharmacology and Experimental Therapeutics* 282(1):44-55.
O'Brien et al. (1996), "Myths About the Treatment of Addiction," *The Lancet* 347:237-240.
Schenk et al. (1999), "U69593, A Kappa-Opioid Agonist, Decreases Cocaine Self-Administration and Decreases Cocaine-Produced Drug-Seeking," *Psychopharmacology* 144:339-346.
Shippenberg et al. (1996), "κ-Opioid Receptor Agonists Prevent Sensitization to the Conditioned Rewarding Effects of Cocaine," *The Journal of Pharmacology and Experimental Therapeutics* 276(2):545-554.
Spangler et al. (1993), "'Binge' Cocaine Administration Induces a Sustained Increase of Prodynorphin mRNA in Rat Caudate-Putamen," *Molecular Brain Research* 19:323-327.
Spangler et al. (1996), "Regulation of Kappa Opioid Receptor mRNA in the Rat Brain by 'Binge' Pattern Cocaine Administration and Correlation with Preprodynorphin mRNA," *Molecular Brain Research* 38:71-76.
Spealman et al. (1992), "Modulation of the Discriminative Stimulus Effects of Cocaine by *Mu* and *Kappa* Opioids," *The Journal of Pharmacology and Experimental Therapeutics* 261(2):607-615.

(Continued)

*Primary Examiner*—San-ming Hui
(74) *Attorney, Agent, or Firm*—Isaac M. Rutenberg; Mintz, Levin, Cohn, Ferris, Glovsky, and Popeo, P.C.

(57) ABSTRACT

A method is provided for treating a drug-dependent individual so as to effect withdrawal from a drug of abuse, e.g., an opiate such as heroin or oxycodone, a stimulant such as cocaine, or alcohol. The method involves substitution therapy wherein a substantially nonaddicting normorphine or norcodeine derivative is substituted for the drug of abuse. The active agent has the structure of formula (I)

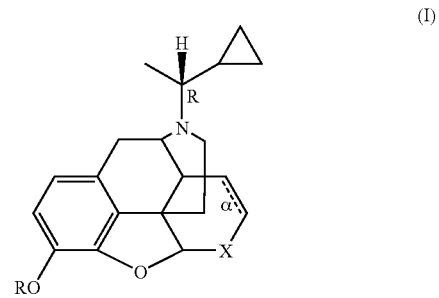

(I)

wherein: R is H, alkyl, or acyl; X is CH(OR') or C=O, wherein R' is H or acyl; α is an optional double bond, with the proviso that when α is present, then X is necessarily CH(OH), or an acid addition salt thereof, wherein preferred such agents are in a stereoisomerically pure form that corresponds to that of N-[(1R)-1-cyclopropylethyl]-normorphine (1) which melts at approximately 188° C.-189° C.

27 Claims, No Drawings

OTHER PUBLICATIONS

Spealman et al. (1994), "Opioid Modulation of the Discriminative Stimulus Effects of Cocaine: Comparison of μ, κ and δ Agonists in Squirrel Monkeys Discriminating Low Doses of Cocaine," *Behavioural Pharmacology* 5:21-31.

Suzuki et al. (1992), "The Role of Mu- and Kappa-Opioid Receptors in Cocaine-Induced Conditioned Place Preference," *Japan. J. Pharmacol*. 58:435-442.

Unterwald et al. (1992), "Chronic Cocaine Alters Brain Mu Opioid Receptors," *Brain Research* 584:314-318.

Unterwald et al. (1994), "Repeated Cocaine Administration Upregulates κ and μ, But Not δ, Opioid Receptors," *NeuroReport* 5(13):1613-1616.

Wang et al. (1999), "Acute Intermittent Morphine Increases Preprodynorphin and Kappa Opioid Receptor mRNA Levels in the Rat Brain," *Molecular Brain Research* 66:184-187.

Yuferov et al. (1999), "Acute 'Binge' Cocaine Increases Mu-Opioid Receptor mRNA Levels in Areas of the Rat Mesolimbic Mesocortical Dopamine System," *Brain Research Bulletin* 48(1):109-112.

Aceto, et al., "Dependence Studies of New Compounds in the Rhesus Monkey, Rat and Mouse (2001)," Natl. Inst. Drug Abuse Research, Monograph, Proc. $63^{rd}$ Ann. Scientific Mtg. UDHHS/NIH (2002) 182:157-210.

\* cited by examiner

TREATMENT OF CHEMICAL DEPENDENCY WITH SUBSTANTIALLY NONADDICTING NORMORPHINE AND NORCODEINE DERIVATIVES

CROSS-REFERENCE TO RELATED APPLICATIONS

This application claims priority under 35 U.S.C. §119(e)(1) to Provisional U.S. Patent Application Ser. No. 60/511,279, filed Oct. 14, 2003. The disclosure of the aforementioned application is incorporated by reference in its entirety.

TECHNICAL FIELD

This invention relates generally to the treatment of chemical dependency. More particularly, the invention relates to the treatment of chemical dependency using substantially nonaddicting derivatives of normorphine and norcodeine, preferably in stereoisomerically pure form.

BACKGROUND

The family of drugs based on N-[(1R)-1-cyclopropylethyl]-normorphine (1) hydrochloride (1.HCl), including various esters at the 6-O-position, has been shown to have high affinities for all three major opiate receptors, i.e., the mu, kappa, and delta receptors. See, e.g., U.S. Pat. No. 4,749,706 to Lawson. However, unlike all other reported opioids, 1 has relatively high efficacy for the kappa receptor and relatively low efficacy for the mu receptor. This unusual profile is demonstrated by several studies on 1 that show strong agonism for pain, modulated through the kappa receptors, but no mu agonism. Thus, 1 has low abuse potential. Remarkably, 1 is also free of punishing kappa agonism effects as well. In studies with rhesus monkeys, 1 has been shown to have a very weak cue for codeine in some concentrations and saline in higher concentration. A unique balance of activities between mu- and kappa-mediated effects that results in a drug without respiratory depression and free of gut transport side effects is also seen. See U.S. Pat. No. 4,749,706 to Lawson; U.S. Pat. No. 4,269,843 to DeGraw et al.; U.S. Pat. No. 4,218,454 to DeGraw et al.; Lawson et al. (1987) *Proceedings of the 48th Meeting of the Committee of Problems in Drug Dependence, NIDA Research Monograph* 76:309; Coop (2000), and Aceto et al. (2000) in *Problems of Dependence: Proceedings of the 62nd Annual Scientific Meeting, the College on Problems of Drug Dependence, inc., NIDA Research Monograph* 181, pp. 109-122, NIDA Publication No. 01-4918, L. S. Harris (Ed).

Addiction to alcohol, cocaine, heroin, and other commonly prescribed pain killers (such as oxycodone, hydrocodone, and the like) continues to be one of the most significant medical, social, and economic problems facing society. These drugs of abuse can induce significant neurochemical and neurophysiological alterations in the brain at cellular and molecular levels, and, in the setting of repeated self-exposure, which can lead to addiction, these changes may be persistent or even permanent. Such altered molecular, cellular, and neurophysiological "set points" in the brain, in turn, contribute to alterations in behavior—with implications for the specific addictive diseases (Kreek (2001) *Ann. N.Y. Acad. Sci.* 937:27-49). Specifically, it has been hypothesized that the endogenous opioid system (EOS), which regulates pleasure and reward in the brain under normal and drug-induced states, is involved in each of the major addictions (Kreek, 2001; Unterwald (2001) *Ann. N.Y. Acad. Sci.* 937:74-92). The EOS consists of various brain structures, cells, cell receptors, and endogenous peptide ligands for these receptors. The brain contains at least four different sets of opioid receptors and their associated peptide ligands. The four types of opioid receptors are known as the mu, kappa, delta, and sigma receptors.

The reinforcing effects of drugs of abuse, generally referred to as "euphoric" effects, lead to craving and make a human being or animal work to obtain drugs for self-administration. The primary sites of action for euphoria-inducing drugs are located in regions of the brain that have abundant dopaminergic terminals, specifically the mesolimbic-mesocortical dopaminergic system and especially the nucleus acumbens, the amygdala, and the anterior cingulate. In addition, the dorsal striatum, which has dopaminergic terminals associated with substantia nigra neurons, is also involved in some components of the behaviors of addiction. Dopamine does not work alone in those areas. Serotonin and other neurotransmitters, as well as neuropeptides, including those of the endogenous opioid system, are also active in these areas.

Dopaminergic neurons of the substantia nigra have projections that release dopamine in the caudate putamen, where there is a close linkage with the opioid system, including both peptides and receptors (Kreek, 2001). Dopaminergic neurons in the ventral tegmental area project to the mesolimbic-mesocortical dopaminergic system, with dopamine release in the nucleus acumbens, amygdala, anterior cingulate, and related regions—again with close connections to the endogenous opioid system.

Importantly, using quantitative techniques, several groups (Branch et al. (1992) *Mol. Brain. Res.* 14:231-238; Spangler et al. (1993) *Mol. Brain Res.* 19:323-7) have mapped the levels of opioid peptide gene expression and found abundant expression of mu- and kappa-acting peptides in the caudate putamen and the nucleus acumbens. Additional studies (Unterwald et al. (1994) *Neuroreport* 15:1613-6; Spangler et al. (1996) *Mol. Brain Res.* 38:71-6; Yuferov et al. (1999) *Brain Res. Bull.* 48:109-12) have found that mu, kappa, and delta receptors are abundantly expressed in the very regions where there are abundant dopaminergic terminal fields.

Opiates: Opiates such as heroin and its chief metabolite, morphine, act initially and specifically at the mu opioid receptor. Heroin and morphine also affect the dopaminergic system by inhibiting GABAergic neurons, which provide the normal inhibitory tone directly modulating dopaminergic neurons in the ventral tegmental area. This inhibition of GABAergic neurons results in increased dopamine release in the nucleus acumbens, amygdala, anterior cingulate, and other parts of the mesolimbic-mesocortical dopaminergic system. Thus, there is a very tight neurochemical connection between the endogenous opioid system and the dopamingergic system mediating the euphoric effects of opiates.

In one model that mimics the most common pattern of opiate abuse, in which morphine is administered in an intermittent, regularly spaced pattern, one group (Wang et al. (1999) *Mol. Brain Res.* 66:184-187) found that both dynorphin and kappa receptor gene expressions were enhanced in whole brains minus the cerebellum. These results suggest a close link between the kappa opioid system and the development of substance dependence to morphine.

Cocaine: Cocaine, in contrast, acts primarily at monoaminergic transporters—the dopamine transporter, the serotonin transporter, and the norepinephrine transporter—to block the normal presynaptic reuptake of neurotransmitters, thus yielding excessive neurotransmitter levels in the perisynaptic region. However, many studies have shown that cocaine significantly alters the endogenous opioid system, too (for review, see Kreek, 2001, cited supra).

A number of animal studies have investigated whether chronic cocaine exposure results in persistent alterations in the endogenous opioid system. Compelling evidence (reviewed in Unterwald et al. 2001, and Kreek, 2001, both cited supra) points to the importance of the mu and kappa opioid receptors in cocaine addiction and craving:

1. Yuferov et al. (1999), supra, showed that binge-pattern cocaine administration significantly alters mRNA levels for the mu opioid receptor in three brain regions only, all of which are linked to mesolimbic-mesocortical dopaminergic outflow—the nucleus acumbens, amygdala, and prefrontal cortex.

2. Unterwald et al. (1992) Brain Res. 584:314-8 has shown that mu receptor density is significantly increased in the anterior cingulate, caudate putamen, nucleus acumbens, and basolateral amygdala after 14 days of binge-pattern cocaine administration.

3. Unterwald et al. (1994), supra, has shown that 14 days of binge-pattern cocaine administration selectively increases the density of kappa opioid receptors, but again only in those dopaminergic fields of the nigrostriatal and mesolimbic-mesocortical dopaminergic systems.

4. Kuzmin et al. (2000) Eur. Neuropsychopharmacol. 10:447-54 demonstrated that multiple opioid receptor systems (i.e., mu and kappa) play a role in reinforcing the properties of cocaine, and that cooperative interaction between mu- and kappa-opioid systems may be important during the initiation of cocaine self-administration.

5. An early study (Mello et al. (1993) Harv. Rev. Psychiatry 1: 168-83) has shown that buprenorphine, an opioid with mixed mu agonist/kappa antagonist character, significantly reduces both opiate and cocaine abuse in patients who had abused these drugs for more than ten years.

6. Two studies using either a chronic 14-day binge-pattern cocaine administration model (Spangler et al., 1993, supra) or a cocaine self-administration model (Daunais et al. (1993) Neuroreport 4:543-6) have shown increased gene expression of dynorphin—an endogenous opioid peptide with activity at kappa opioid receptors—in the caudate putamen. Other studies (Yuferov et al., 1999, supra) have shown that acute, subacute, and chronic cocaine administration enhances dynorphin gene expression.

Alcohol: Alcohol has also been shown to possibly alter both neurotransmitter and neuropeptide systems, including the dopaminergic and the endogenous opioid systems (for review, see Kreek, 2001).

Owing to the native role of the endogenous opioid system in pleasure and reward responses and to its alterations in chemical dependency and addiction, a number of opiates have been used with some success to treat addictions to opiates and/or alcohol. For example, it is known from many studies that heroin addiction in animals and humans may be satisfactorily treated with opioid drugs, specifically mu antagonists (e.g., naltrexone and nalmefene), long-acting and low- or partial-efficacy mu agonists (e.g., methadone and buprenorphine), and selective kappa agonists) See, for example: Mello et al. (1982) J. Pharmacol. Exp. Ther. 223:30-9; Bickel et al. (1988) Clin. Pharmacol. Therapeut. 43:72-8; Johnson et al. (1992) Jour. Amer. Med. Assoc. 267:2750-5; Robinson et al. (1993) Drug Alcohol Depen. 33:81-6; Meandzija et al. (1994) in: N. S. Miller, Ed., The principles and practice of addictions in psychiatry (Section XII, Chapter 4, pp. 1-5)(Philadelphia, Pa.: W. B. Saunders Company); Strain (1994) Amer. Jour. Psychiat. 151:1025-30; Jaffee et al. (1995) Psychiat. Ann. 25: 369-75; Herman et al. (1996) paper presented at the American Academy of Child and Adolescent Psychiatry, Philadelphia, Pa.; O'Brien et al. (1996) The Lancet 347:237-40. Litten et al. (1997) in N. S. Miller, Ed., The principles and practice of addictions in psychiatry (pp. 532-567) (Philadelphia, Pa.: W. B. Saunders Company); and Litten et al. (1999) J. Substance Abuse Treat 16:105-12. The latter reference also describes the successful use of naltrexone, a general opiate antagonist, for the treatment of alcoholism.

Currently, no pharmacotherapies are commercially available for cocaine addiction (see Litten et al., 1999). A number of different drugs are in development for this purpose, including buprenorphine, an opiate. However, a number of experimental studies have demonstrated that other opiates, particularly kappa-agonists, are effective in blocking cocaine-dependent responses such as drug preference and discrimination, self-administration, scheduled-controlled responding, and cocaine-induced hypersensitivity in animals. See Spealman et al. (1992) J. Pharmacol. Exp. Ther. 261:607-15; Spealman et al. (1 994) Behav. Pharmacol. 5:21-31; Suzuki et al. (1992) Jpn. J. Pharmacol. 58:435-42; Ukai et al. (1994) Yakubutsu Seishin Kodo 14:153-9; Crawford et al. (1995) Psychopharmacol. 120:392-9; Shippenerg et al. (1996) J. Pharmacol. Exp. Therap. 276:545-54; Negus et al. (1997) J. Pharm. Exper. Ther. 282(2):44-55; Mello et al. (1998) J. Pharm. Exper. Therap. 286(2):812-814; and Schenk et al. (1999) Psychopharmcol. 144:339-46.

These results suggest that activation of kappa opioid receptors may functionally antagonize some abuse-related effects of cocaine, possibly by inhibiting the release of dopamine from dopaminergic neurons.

SUMMARY OF THE INVENTION

The invention relates to a method for treating a drug-dependent individual, comprising administering to the individual a therapeutically effective amount of a pharmacologically active agent having the structure of formula (I)

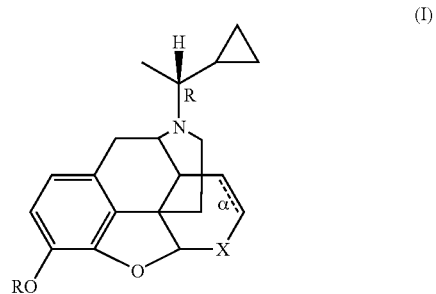

wherein:
R is H, alkyl, or acyl;
X is CH(OR') or C=O, wherein R' is H or acyl;
α is an optional double bond, with the proviso that when α is present, then X is
necessarily CH(OH),
or an acid addition salt thereof.

Preferred compounds of formula (I) are those in a stereoisomerically pure form corresponding to that of N-[(1R)-1-cyclopropylethyl]-normorphine which melts at approximately 188° C.-189° C. In this compound, the α-carbon atom has the R configuration.

It has now been found that compounds of formula (I) substitute completely for morphine in morphine-dependent individuals without any dependence liability to individuals who are not dependent on morphine or other mu-acting opiates. Also, in rhesus monkey studies, these compounds have been shown to have a very weak cue for codeine at relevant concentrations and saline in higher concentration. In other words, the compounds can mimic a mu-acting drug like morphine or codeine without causing a dependence liability, unlike morphine. Finally, the compounds can be used safely, since unlike mu-acting drugs, 1 has been shown in animals to be free of respiratory depression and to have a high therapeutic index. See Coop et al. (2001), supra, and U.S. Pat. No. 4,749,706 to Lawson.

The combination of strong kappa agonism, mild delta agonism, and weak mu antagonism in compounds of formula (I) constitutes a unique and unprecedented profile for an opioid drug and has produced a non-addicting substitute for morphine and other commonly prescribed opiate drugs that act primarily via the mu receptor.

Moreover, the significant kappa-agonism of these compounds suggests that they will be useful for treating patients chemically dependent upon cocaine. The compounds are expected to be more improved relative to other, more selective kappa agonists, since these drugs possess punishing side effects not associated with the administration of compounds of formula (I). Finally, the mu antagonist character of these compounds suggests that they will useful for treating alcoholism.

Thus, compounds of formula (I) are unprecedented, non-toxic, orally active opiates that may be applied to successfully treat patients addicted to heroin and other opiates, cocaine, and/or alcohol. The compounds can be used to re-set the endogenous opioid system and restore neurochemical balance in patients dependent upon or addicted to opiates, cocaine, and alcohol. Treatment with the present compounds will serve to up-regulate and restore levels of mu receptors and endogenous ligands in important pleasure-reward brain circuits. Proper re-setting of these mechanisms will increase the likelihood for successful weaning of the addict, quicken the time to weaning, and reduce the incidence of recidivism to drug-taking behavior.

The absence of dependence liability in 1 (Coop, 2001, supra) makes it superior to other opiates, such as methadone, levomethadyl acetate (LAAM), or buprenorphine, that are used for treating addiction to opiates. These drugs suffer from dependence liability, due to their predominant agonist activities at mu opioid receptors. The dependence liability of these drugs imposes certain limits on how they may be used to treat dependence to opiates and other addictive substances.

Also, unlike methadone, LAAM, and buprenorphine, compounds of formula (I) display activities at not one or two but rather three different opioid receptors. As a result, compounds of formula (I) exhibit a more global, less selective profile of action than is commonly found for other, conventionally used opiates. Since addictions to opiates, cocaine, and alcohol are complex neurochemical processes involving multiple receptors (including opioid receptors) and transporters in the brain, an opiate with a more global, less selective mechanism of action is highly preferable. A less selective, more globally active opiate such as those used in conjunction with the present invention will interact with a greater number and diversity of opioid receptors, which, in turn, leads to a more thorough re-setting of brain opioid circuits that have been altered during the development of substance dependence and addiction.

DETAILED DESCRIPTION OF THE PREFERRED EMBODIMENTS

Unless otherwise indicated, the invention is not limited to specific synthetic methods, analogs, substituents, pharmaceutical formulations, formulation components, modes of administration, or the like, as such may vary. It is also to be understood that the terminology used herein is for the purpose of describing particular embodiments only and is not intended to be limiting.

As used in the specification and the appended claims, the singular forms "a," "an," and "the" include plural referents unless the context clearly dictates otherwise. Thus, for example, reference to "a substituent" includes a single substituent as well as two or more substituents that may be the same or different, reference to "a compound" encompasses a combination or mixture of different compounds as well as a single compound, reference to "a pharmaceutically acceptable carrier" includes two or more such carriers as well as a single carrier, and the like.

In this specification and in the claims that follow, reference will be made to a number of terms, which shall be defined to have the following meanings:

As used herein, the phrase "having the formula" or "having the structure" is not intended to be limiting and is used in the same way that the term "comprising" is commonly used.

The term "alkyl" as used herein refers to a branched or unbranched saturated hydrocarbon group typically although not necessarily containing 1 to about 24 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl, and the like. Generally, although again not necessarily, alkyl groups herein contain 1 to about 18 carbon atoms, preferably 1 to about 12 carbon atoms. The term "lower alkyl" intends an alkyl group of 1 to 6 carbon atoms. Preferred substituents identified as "$C_1$-$C_6$ alkyl" or "lower alkyl" contain 1 to 3 carbon atoms, and particularly preferred such substituents contain 1 or 2 carbon atoms (i.e., methyl and ethyl). "Substituted alkyl" refers to alkyl substituted with one or more substituent groups, and the terms "heteroatom-containing alkyl" and "heteroalkyl" refer to alkyl in which at least one carbon atom is replaced with a heteroatom, as described in further detail infra. If not otherwise indicated, the terms "alkyl" and "lower alkyl" include linear, branched, cyclic, unsubstituted, substituted, and/or heteroatom-containing alkyl or lower alkyl, respectively.

The term "aryl" as used herein, and unless otherwise specified, refers to an aromatic substituent containing a single aromatic ring or multiple aromatic rings that are fused together, directly linked, or indirectly linked (such that the different aromatic rings are bound to a common group such as a methylene or ethylene moiety). Preferred aryl groups contain 5 to 20 carbon atoms, and particularly preferred aryl groups contain 5 to 14 carbon atoms. Exemplary aryl groups contain one aromatic ring or two fused or linked aromatic rings, e.g., phenyl, naphthyl, biphenyl, diphenylether, diphenylamine, benzophenone, and the like. "Substituted aryl" refers to an aryl moiety substituted with one or more substituent groups, and the terms "heteroatom-containing aryl" and "heteroaryl" refer to aryl substituent, in which at least one carbon atom is replaced with a heteroatom, as will be described in further detail infra. If not otherwise indicated, the term "aryl" includes unsubstituted, substituted, and/or heteroatom-containing aromatic substituents.

The term "aralkyl" refers to an alkyl group with an aryl substituent, wherein "aryl" and "alkyl" are as defined above. Preferred aralkyl groups contain 6 to 24 carbon atoms, and particularly preferred aralkyl groups contain 6 to 16 carbon atoms. Examples of aralkyl groups include, without limitation, benzyl, 2-phenyl-ethyl, 3-phenyl-propyl, 4-phenyl-butyl, 5-phenyl-pentyl, 4-phenylcyclohexyl, 4-benzylcyclohexyl, 4-phenylcyclohexylmethyl, 4-benzylcyclohexylmethyl, and the like.

The term "acyl" refers to substituents having the formula —(CO)-alkyl, —(CO)-aryl, or —(CO)-aralkyl, and the term "acyloxy" refers to substituents having the formula —O(CO)-alkyl, —O(CO)-aryl, or —O(CO)-aralkyl, wherein "alkyl," "aryl", and "aralkyl" are as defined above.

"Optional" or "optionally" means that the subsequently described circumstance may or may not occur, so that the description includes instances where the circumstance occurs and instances where it does not. For example, the phrase "optional double bond" means that two atoms may or may not be linked through a double bond, and, thus, the description includes molecular segments wherein the two atoms are linked through a double bond and molecular segments wherein the two atoms are linked through only a single bond.

When referring to an active agent used in conjunction with the method of the invention, it is intended that the term "active agent" or "compound" encompass not only the specified molecular entity but also its pharmaceutically acceptable, pharmacologically active analogs, including, but not limited to, salts, esters, prodrugs, conjugates, active metabolites, and other such derivatives, analogs, and related compounds.

By "pharmaceutically acceptable" is meant a material that is not biologically or otherwise undesirable, i.e., the material may be incorporated into a pharmaceutical composition administered to a patient without causing any undesirable biological effects or interacting in a deleterious manner with any of the other components of the composition in which it is contained. When the term "pharmaceutically acceptable" is used to refer to a pharmaceutical carrier or excipient, it is implied that the carrier or excipient has met the required standards of toxicological and manufacturing testing or that it is included on the Inactive Ingredient Guide prepared by the U.S. Food and Drug administration. "Pharmacologically active" (or simply "active") as in a "pharmacologically active" derivative or analog, refers to a derivative or analog having the same type of pharmacological activity as the parent compound and approximately equivalent in degree.

Normorphine and norcodeine have the formula (II)

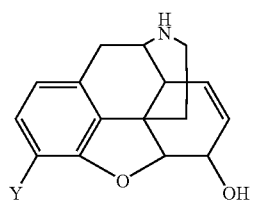
(II)

In normorphine, Y is OH, and in norcodeine, Y is $OCH_3$. It is known that certain conversions in the cyclohexene ring of codeine and morphine do not destroy biological activity. Specifically, the compound can be treated with a suitable reducing agent, such as hydrogen, to remove the double bond. The resulting cyclohexanol analog is active, and it can be oxidized to provide the cyclohexanone derivative, which is also active. The foregoing are referred to collectively herein as "conventional analogs." Hence, although the examples herein describe the preparation of N-α-methylcyclopropylmethyl-normorphine and the separation of the compound into its individual diastereomers, the compound or its diastereomers can be converted using the manipulations of the cyclohexenol ring shown in structure (II). Also, the OH of ring (3) can be methylated to obtain the corresponding codeine-related analogs. Methods for methylation are known in the art, for example, using phenyltrimethylammonium hydroxide (see German Pat. No. 247,180 (1909)) and using the corresponding ethoxide (Rodinor (1929) *Bull Soc Chim* 39:305).

By "stereoisomerically pure" is meant the diastereomer has the R configuration at the α-carbon of the methylcyclopropylmethyl substituent. As described in U.S. Pat. No. 4,749,706 to Lawson, the R-diastereomer of N-methylcyclopropylmethyl-normorphine is significantly more active (about 25 times) than the other diastereomer. Therefore, the stereoisomerically pure forms of the invention will be referred to that of the normorphine derivative that has the R configuration alpha to the N-atom.

The active agents used to treat drug-dependent individuals according to the present invention have the structure of formula (I)

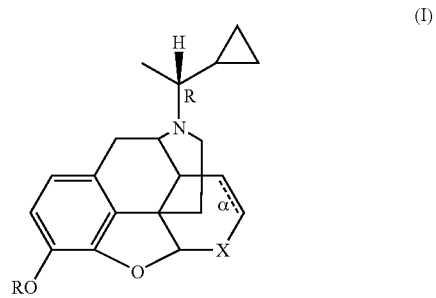
(I)

wherein:
R is H, alkyl, or acyl;
X is CH(OR') or C=O, wherein R' is H or acyl; and
α is an optional double bond, with the proviso that when α is present, then X is necessarily CH(OH).

The active agent is preferably in a stereoisomerically pure form that corresponds to that of N-[(1R)-1-cyclopropyl-ethyl]-normorphine which melts at approximately 188° C.-189° C.

Preferably, R is H, $C_1$-$C_6$ alkyl, or acyl, wherein the acyl group is of the formula —(CO)—$R^1$ in which $R^1$ is $C_1$-$C_6$ alkyl, $C_5$-$C_{14}$ aryl, or $C_6$-$C_{16}$ aralkyl. More preferably, R is H, methyl, or benzyl.

Preferred X groups are CH(OH) and CH(O-acyl), with the latter groups exemplified by CH(O—CO—$R^1$) in which $R^1$ is $C_1$-$C_6$ alkyl, $C_5$-$C_{14}$ aryl, or $C_6$-$C_{16}$ aralkyl. More preferred X groups are CH(OH) and CH(O—CO-benzyl).

Most preferred compounds are wherein R is methyl, X is CH(OR'), R' is H, and α is either present or absent.

A compound of the invention may be administered in the form of a salt, ester, prodrug, active metabolite, analog, or the like, provided that the salt, ester, prodrug, active metabolite or analog is pharmaceutically acceptable and pharmacologically active in the present context. Salts, esters, prodrugs, active metabolites, analogs, and other derivatives of the active agents may be prepared using standard procedures known to those skilled in the art of synthetic organic chemistry and described, for example, by J. March, Advanced Organic Chemistry: Reactions, Mechanisms and Structure, 4th Ed. (New York: Wiley-Interscience, 1992).

For example, acid addition salts may be prepared from the free base using conventional methodology involving reaction of the free base with an acid. Suitable acids for preparing acid addition salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, e.g., hydrochloric acid, hydrobromic acid, sulfuric acid, nitric acid, phosphoric acid, and the like. An acid addition salt may be reconverted to the free base by treatment with a suitable base. Prodrugs, conjugates, and active metabolites may also be prepared using techniques known to those skilled in the art or described in the pertinent literature. Prodrugs and conjugates are typically prepared by covalent attachment of a moiety that results in a compound that is therapeutically inactive until modified by an individual's metabolic system.

Other derivatives and analogs of the active agents may be prepared using standard techniques known to those skilled in the art of synthetic organic chemistry, or may be deduced by reference to the pertinent literature.

As described in U.S. Pat. No. 4,749,706 to Lawson, the compounds used in the method of the invention are prepared in stereoisomerically pure form by separating the desired pure diastereomers (R and S configurations) from the mixture of the N-methylcyclopropylmethyl-normorphine diastereomers, and effecting additional conversions, if necessary, from the stereoisomerically pure forms. The N-[1(R,S)-1-cyclopropylethyl]-normorphine mixture is first converted to a mixture of the diesters by reaction with a monocarboxylic acid. The esters are generally prepared from the corresponding acyl halides, which are, in turn, obtained from the free acid using an inorganic halide such as thionyl chloride or phosphorus pentachloride, as is understood in the art. The esterification is conducted in a suitable solvent medium containing a mild base such as, for example, pyridine, an alkylpyridine, or a trialkylamine, preferably pyridine, using as excess of the acyl halide. The resulting diesters are purified from the reaction mixture, if desired, using general standard work-up procedures.

The diastereomeric mixture of the diester is then subjected to separation into its stereoisomerically pure forms using conventional techniques known in the art, for example, chromatography on columns, or on thin layer plates, or using HPLC or differential crystallization. The precise nature of the separation method employed will depend on which diester of the normorphine derivative is chosen. For the dibenzoate, a convenient and preferred diester, differential crystallization is preferred. In this case, the more active isomer crystallizes readily from a solution containing both diastereomeric forms.

The mixture of the N-α-methylcyclopropylmethyl-normorphine diastereomers can be prepared in the manner described in U.S. Pat. No. 4,269,843 or 4,218,454, cited above.

Compounds used herein may also be prepared according to an improved method of N-substitution disclosed in U.S. Pat. No. 4,749,706, according to N-α-methylcyclopropylmethyl-normorphine or other N-substituted derivatives of normorphine, norcodeine and analogs thereof may be obtained. In the improved method, the desired N-α-methylalkylmethyl group is supplied as the alkyl methyl ketone of the formula $RCOCH_3$, wherein R is alkyl as herein defined. The ketone is added to the normorphine or norcodeine or conventional analog in the presence of a reducing agent, such as, for example, an alkali metal cyanoborohydride or borohydride, or catalytic hydrogenation, preferably using sodium cyanoborohydride, either directly to a mixture of the compounds or in the presence of an aprotic solvent. The reaction is conducted at about 50° C.-100° C. over the course of 10 minutes to 3 hours, preferably around 30 minutes. The reaction is quenched with weak acid to remove excess reducing agent.

As noted above, the method of the invention is intended to enable a drug-addicted individual to discontinue use of the abused drug without experiencing intense craving for that drug or severe physiological withdrawal symptoms.

The present method is useful for effecting withdrawal from a wide range of drugs possessing addictive properties. The method is useful, for example, useful in treating an individual withdrawing from a narcotic, e.g., from an opiate such as alfentanil, buprenorphine, butorphanol, codeine, fentanyl, heroin, hydrocodone, hydromorphone, levorphanol, meperidine, methadone, morphine, nalbuphine, oxycodone, oxymorphone, pentazocine, propoxyphene, sufentanil, or tramadol. The method also extends to treatment of an individual who is addicted to a stimulant such as cocaine, or who is alcohol-dependent.

It is intended that an active agent as described above be administered as a substitute for the abused drug. Thus, at the beginning of the treatment period, the active agent will be administered in an amount effective to achieve as nearly as possible the psychic and physiological effects experienced with the drug of abuse, with the amount of the active agent administered gradually decreased over the treatment period. Typically, this involves administration of a therapeutically effective amount of the active agent at least once every twenty-four hours. By "therapeutically effective amount" is intended a dosage quantity effective to significantly alleviate craving for the drug of abuse as well as reducing the intensity of or eliminating withdrawal symptoms associated with its discontinuance. The total treatment period will normally be at least about two weeks, preferably at least about four weeks, and possibly much longer, e.g., up to a year or more, if psychic withdrawal symptoms persist.

The amount of active agent administered will, of course, be dependent on the subject being treated, the severity of the addiction, the manner of administration, and the judgment of the prescribing physician. However, an effective dosing regimen will generally involve administration of approximately 0.1 to 0.5 mg/kg/day, preferably about 0.2 mg/kg/day. Gradual reduction in dosage throughout the treatment period for an average 70 kg human would amount to 7-35 mg/day, or preferably about 14 mg/day. It is usually desirable to begin reducing the dosage at some point during the treatment period, so that discontinuance of the active agent is gradual and tapered. The length of the "tapering off" period will vary, clearly, with the individual undergoing treatment, the drug of abuse, the severity of the affliction, and the like. Reduction in dosage will generally not be initiated prior to two weeks into the treatment period.

The active agent may be administered orally, parenterally, rectally, vaginally, buccally, sublingually, nasally, by inhalation, topically, transdermally, or via an implanted reservoir in dosage forms containing conventional non-toxic pharmaceutically acceptable carriers and excipients. The term "parenteral" as used herein is intended to include subcutaneous, intravenous, and intramuscular injection. Depending on the intended mode of administration, the pharmaceutical formulation may be a solid, semi-solid or liquid, such as, for example, a tablet, a capsule, a caplet, a liquid, a suspension, an emulsion, a suppository, granules, pellets, beads, a powder, or the like, preferably in unit dosage form suitable for single administration of a precise dosage. Suitable pharmaceutical compositions and dosage forms may be prepared using conventional methods known to those in the field of pharmaceutical formulation and described in the pertinent texts and literature, e.g., in Remington: The Science and Practice of Pharmacy, cited above.

For those compounds that are orally active, oral dosage forms are generally preferred, and include tablets, capsules, caplets, solutions, suspensions and syrups, and may also comprise a plurality of granules, beads, powders or pellets that may or may not be encapsulated. Preferred oral dosage forms are tablets and capsules.

Tablets may be manufactured using standard tablet processing procedures and equipment. Direct compression and granulation techniques are preferred. In addition to the active agent, tablets will generally contain inactive, pharmaceutically acceptable carrier materials such as binders, lubricants, disintegrants, fillers, stabilizers, surfactants, coloring agents, and the like. Binders are used to impart cohesive qualities to a tablet, and thus ensure that the tablet remains intact. Suitable binder materials include, but are not limited to, starch (including corn starch and pregelatinized starch), gelatin, sugars (including sucrose, glucose, dextrose, and lactose), polyethylene glycol, waxes, and natural and synthetic gums, e.g., acacia sodium alginate, polyvinylpyrrolidone, cellulosic polymers (including hydroxypropyl cellulose, hydroxypropyl methylcellulose, methyl cellulose, microcrystalline cellulose, ethyl cellulose, hydroxyethyl cellulose, and the like), and Veegum. Lubricants are used to facilitate tablet manufacture, promoting powder flow and preventing particle capping (i.e., particle breakage) when pressure is relieved. Useful lubricants are magnesium stearate, calcium stearate, and stearic acid. Disintegrants are used to facilitate disintegration of the tablet, and are generally starches, clays, celluloses, algins, gums, or crosslinked polymers. Fillers include, for example, materials such as silicon dioxide, titanium dioxide, alumina, talc, kaolin, powdered cellulose, and microcrystalline cellulose, as well as soluble materials such as mannitol, urea, sucrose, lactose, dextrose, sodium chloride, and sorbitol. Stabilizers, as well known in the art, are used to inhibit or retard drug decomposition reactions that include, by way of example, oxidative reactions.

Capsules are also preferred oral dosage forms, in which case the active agent-containing composition may be encapsulated in the form of a liquid or solid (including particulates such as granules, beads, powders or pellets). Suitable capsules may be either hard or soft, and are generally made of gelatin, starch, or a cellulosic material, with gelatin capsules preferred. Two-piece hard gelatin capsules are preferably sealed, such as with gelatin bands or the like. See, for example, Remington: The Science and Practice of Pharmacy, cited supra, which describes materials and methods for preparing encapsulated pharmaceuticals.

Oral dosage forms, whether tablets, capsules, caplets, or particulates, may, if desired, be formulated so as to provide for gradual, sustained release of the active agent over an extended time period. Generally, as will be appreciated by those of ordinary skill in the art, sustained release dosage forms are formulated by dispersing the active agent within a matrix of a gradually hydrolyzable material such as an insoluble plastic (e.g., polyvinyl chloride or polyethylene), or a hydrophilic polymer, or by coating a solid, drug-containing dosage form with such a material. Hydrophilic polymers useful for providing a sustained release coating or matrix include, by way of example: cellulosic polymers such as hydroxypropyl cellulose, hydroxyethyl cellulose, hydroxypropyl methyl cellulose, methyl cellulose, ethyl cellulose, cellulose acetate, and carboxymethylcellulose sodium; acrylic acid polymers and copolymers, preferably formed from acrylic acid, methacrylic acid, acrylic acid alkyl esters, methacrylic acid alkyl esters, and the like, e.g. copolymers of acrylic acid, methacrylic acid, methyl acrylate, ethyl acrylate, methyl methacrylate and/or ethyl methacrylate; and vinyl polymers and copolymers such as polyvinyl pyrrolidone, polyvinyl acetate, and ethylene-vinyl acetate copolymer.

Preparations according to this invention for parenteral administration include sterile nonaqueous solutions, suspensions, and emulsions. Examples of nonaqueous solvents or vehicles are propylene glycol, polyethylene glycol, vegetable oils, such as olive oil and corn oil, gelatin, and injectable organic esters such as ethyl oleate. Parenteral formulations may also contain adjuvants such as preserving, wetting, emulsifying, and dispersing agents. The formulations are rendered sterile by incorporation of a sterilizing agent, filtration through a bacteria-retaining filter, irradiation, or heat. They can also be manufactured using a sterile injectable medium.

The active agent may also be administered through the skin or mucosal tissue using a conventional transdermal drug delivery system, wherein the active agent is contained within a laminated structure that serves as a drug delivery device to be affixed to the skin. In such a structure, the drug composition is contained in a layer, or "reservoir," underlying an upper backing layer.

Although the present compositions will generally be administered orally, parenterally, or transdermally, other modes of administration are suitable as well. For example, administration may be rectal, preferably using a suppository that contains, in addition to the active agent, excipients such cocoa butter or a suppository wax. Formulations for nasal or sublingual administration are also prepared with standard excipients well known in the art. The pharmaceutical compositions of the invention may also be formulated for inhalation, e.g., as a solution in saline, as a dry powder, or as an aerosol.

It is to be understood that while the invention has been described in conjunction with the preferred specific embodiments thereof, the description above as well as the examples that follow are intended to illustrate and not limit the scope of the invention. Other aspects, advantages and modifications within the scope of the invention will be apparent to those skilled in the art to which the invention pertains.

All patents, patent applications, journal articles, and other references cited herein are incorporated by reference in their entireties.

EXAMPLE 1

Preparation of
N-[(1R,S)-1-Cyclopropylethyl]-Norcodeine as a Diastereomeric Mixture A solution of 25.3 g (0.066 mol) of N-(1-cyano)-1-ethyl-norcodeine (DeGraw et al. (1978) *J. Med Chem* 21: 495) in 155 mL of THF was slowly added to a solution of cyclopropyl magnesium bromide (from 49.2 g, 0.41 mol of cyclopropyl bromide and 25 g of magnesium) in 750 mL of THF. After 30 min the mixture was poured into 500 mL of 1N HCl and washed with 200 mL of $Et_2O$. The aqueous portion was made strongly alkaline with conc. $NH_4OH$ and extracted with 250 mL of $CH_2Cl_2$. The extract was dried ($MgSO_4$) and evaporated to leave 16.1 g of crude product. The material was taken up in 100 mL EtOAc-EtOH (95:5) and filtered through 400 g of silica gel in a Buchner filter. The adsorbent was eluted with 3 L of the solvent followed by evaporation of the filtrate to leave 11.8 g (51%) of a yellow gum; TLC (silica gel, EtOAc-EtOH-$Et_3N$, 17:2:1) showed a single UV and $I_2$ absorbing spot at $R_f$ 0.50; representing the title compounds as a mixture of diastereomers. NMR ($CDCl_3$): δ 0.60 (5H, m, cyclopropyl), 1.25 (3H, d, $CH_3$—CH), 3.80 (3H, s, $OCH_3$), 4.90 (1H, d, $C_5$—H), 6.50 (1H, d, $C_1$—H), 6.70 (1H, d, $C_2$—H).

EXAMPLE 2

Preparation of
N-[(1R,S)-1-Cyclopropylethyl]-Normorphine as a
Diastereomeric Mixture A. To convert the norcodeine derivative prepared in Example 1 to the normorphine derivative, a solution of 24.7 g (0.07 mol) of N-α-methylcyclopropylmethyl-norcodeine in 500 mL of dry tetrahydrofuran was treated with 25 g (0.13 mol) of diphenylphosphine and cooled to 0° C.-5° C. in an ice bath. Then 135 mL of 1.4N butyl lithium in hexane was added rapidly by syringe. The mixture was allowed to warm to room temperature and then stirred at reflux for 30 min. The reaction was cooled and quenched by the slow addition of 100 mL of 2N HCl. The solvents were evaporated in vacuo and the aqueous portion was made strongly alkaline by the addition of 2N NaOH and again washed with 200 mL of ether. The pH was adjusted to 8-9 and the mixture extracted twice with 200 mL portions $CH_2Cl_2$. The extract was dried ($MgSO_4$) and evaporated in vacuo to leave 10.7 g of the crude free base. The material was chromatographed on 600 g of silica gel to afford 8.0 g (47%) of purified base.

The title hydrochloride salt was prepared in methanol and recrystallized from methanol/N-octanol, 1:7, mp 248° C.-250° C. NMR ($CD_3OD$) δ 0.40 ($^1H$), m, cyclopropyl-H), 0,85 (4H, m, cyclopropyl $CH_2$), 1.62 (3H, d, $CH_3CH$), 4.94 (1H, d, $C_5$—H), 5.35, 5.75 (2H, d, $C_7$-$C_8$H's), 6.50 (1H, d $C_1$—H), 6.65 (1H, d, $C_2$—H); $^{13}$C-NMR ($CD_3OD$-DCI) δ 66.38, 65.32 ($C_2$'), 58.28, 58.17 ($C_9$), 23.84, 22.65 ($C_1$'). Signal heights indicated a 50:50 mixture of R and S isomers at $C_{17}$. Anal. for $C_{21}H_{25}NO_3HCl.H_2O$: Calc'd. C, 64.0; H, 7.12; N, 3.56; Found: C, 64.3; H, 6.99; N, 3.46.

B. In an alternative method, the normorphine derivative was directly prepared by the improved method of the invention as follows: A stirred suspension of 8.0 g (26 mM) of normorphine in 25 mL of methylcyclopropylketone and 2.5 ml of acetic acid at 70° C. was treated with 4.0 g (64 mM) of $NaBH_3CN$ in four equal portions over 30 min. After $H_2$ evolution ceased, the solution was cooled and glacial HOAc added dropwise until excess $NaBH_3CN$ was quenched. The mixture was then partitioned between 100 mL of 3N HCl and 20 mL of $Et_2O$. The acid extract was alkalized to pH 8-9 with con $NH_4OH$ and extracted twice with 150 ml portions of $Et_2O$. The $Et_2O$ was dried over $MgSO_4$ and evaporated to leave a partially crystalline residue. Trituration with $Et_2O$/MeOH (9:1) was followed by collection of product to afford 5.0 g (66%) of the stereoisomeric mixture set forth in the title. NMR and chromatographic properties were identical to material prepared by Method A.

EXAMPLE 3

Preparation of N-[(1R)-1-Cyclopropylethyl]-Normorphine Dibenzoate and N-[(1S)-1-Cyclopropylethyl]-Normorphine Dibenzoate The solution of the diastereomeric mixture prepared in Example 2 (5.0 g, 14.7 mM) in 50 mL of pyridine was treated dropwise with 6.1 g (43 mM) of benzoyl chloride was maintenance of the temperature at or below 50° C. After 30 min the mixture was treated with 5 mL of $CH_3OH$ and evaporated in vacuo. The residue was partitioned between 100 mL of $CH_2Cl_2$ and 50 mL of 3N HCl. The $CH_2Cl_2$ extract (containing the product) was washed with saturated $NaHCO_3$ (50 mL) and dried over $MgSO_4$. After filtration through a short pad of silica gel (50 g) with elution by EtOAc, the solvent was removed in vacuo to leave 6.3 g (86%) of a yellow gum. The mixture was separated by preparative HPLC on silica gel with elution by EtOAc:hexane:$CH_3OH$, 9:9:2). The enriched fractions were combined and evaporated to afford the A diastereomer (2.20 g, 35%) and B diastereomer (2.03 g, 32%). Each was crystallized from $CH_2Cl_2$/cyclohexane to give white crystals.

N-methylcyclopropylmethyl-normorphine dibenzoate (diastereomer A), mp 129-130.5, solidified, remelts 162°-164° C. NMR ($CDCl_3$) δ 0.1 and 0.8 (5H, m cyclopropyl), 1.30 (3H, d, $CH_3$), 1.8-2.9 (7H, m, $C_{10}$, $C_{14}$, $C_{15}$, $C_{16}$, $C_{19}$ H's), 3.10 (1H, d, C-16H), 4.30 (1H, m, C-9H), 5.30 (1H, m, C-6H), 5.40 (1H, C-7H), 5.70 (1H, d, C-8H), 6.70 (1H, d, C-1H), 7.00 (1H, d, C-2H), 7.40 (6H, m, benzoate), 8.1 (4H, m, benzoate). Anal. $C_{35}H_{33}NO_5$: Calc'd. C, 76.8; H, 6.03; N, 2.56; Found: C, 77.0; H, 5.99; N, 2.48.

Diastereomer B of N-methylcyclopropylmethyl-normorphine dibenzoate, mp 126°-128° C. (softens), solidifies and remelts 155°-159° C.; NMR ($CDCl_3$): same as noted for the A-diastereomer except for the C-9H at δ 3.85 and C-16H at 3.50.

The isomers could be distinguished by TLC on silica gel, EtOAc-hexane-$CH_3OH$ (7:7:1) with the A form at $R_f$ 0.48 and the B form $R_f$ 0.41.

EXAMPLE 4

Protection Group Removal from the Separated
Diastereomers

A solution of 1.0 g (1.83 mM) of N-methylcyclopropylmethyl-normorphine dibenzoate (diastereomer A) or its B isomer in 25 mL of 1.5N KOH in $CH_3OH$ was heated to reflux and kept at reflux for 5 min. The pH was adjusted to 9 by addition of 3N HCl and the mixture was evaporated to remove $CH_3OH$. The residue was partitioned between 50 mL of $Et_2O$ and 50 mL of $H_2O$, followed by 2 additional extractions by 50 mL portions of $Et_2O$. The combined $Et_2O$ extracts were dried ($MgSO_4$) and evaporated to leave white crystalline residues.

N-methylcyclopropylmethyl-normorphine (1, R isomer) (0.49 g, 80%), mp 188°-189° C. NMR ($CDCl_3$) δ 0.05-0.80 (5H, m cyclopropyl), 1.25 (3H, d, $CH_3$), 1.86 (2H, m, C-15H, C-17H), 2.04 (1H, m, C-15H), 2.33 (2H, m, C-16H, C-10H), 2.64 (1H, s, C-14H), 2.85 (1H, d, C-10H), 3.04 (1H, d, C-10H), 3.93 (1H, m, C-16H), 4.10 (1H, m, C-6H), 4.20 (1H, m, C-9H), 4.80 (1H, d, C-5H), 5.24 (1H, m, C-7H), 5.60 (1H, d, C-8H), 6.42 (1H, d, C-1H), 6.54 (1H, d, C-2H).

N-methylcyclopropylmethyl-normorphine (diastereomer B) (0.51 g, 82%), mp 209°-210° C. NMR ($CDCl_3$) δ 0.05-0.80 (5H, m, cyclopropyl), 1.26 (3H, d, $CH_3$), 1.69 (1H, m, C-17H), 1.92 (1H, d, C-15H), 2.02 (1H, t, C-15H), 2.30 (2H, m, C-16H, C-10H), 2.62 (1H, br s, C-14H), 2.84 (1H, d, C-10H), 3.44 (1H, br d, C-16H), 3.71 (1H, br s, C-9H), 4.13 (1H, br s, C-6H), 4.87 (1H, d, C-5H), 5.24 (1H, m, C-7H), 5.65 (1H, d, C-8H), 6.44 (1H, d, C-1H), 6.62 (1H, d, C-2H).

Conversion to HCl salts by treatment with methanolic HCl followed by recrystallization for $CH_2Cl_2$-$Et_2O$ gave N-methylcyclopropylmethyl-normorphine.HCl (1.HCl) 0° C. (dec.); N-methylcyclopropylmethyl-normorphine HCl (diastereomer B), mp 200°-205° C.

EXAMPLE 5

Biological Activity

Antagonist activity, considered a measure of nonaddictiveness, was measured by the opiate receptor assay of Pert et al.

(1974) *Mol. Pharmacol.* 10:868. Antagonist activity was also measured using the induced Straub tail method as described by DeGraw et al. (1978) *J. Med Chem.* 21:415, and Blumberg et al. (1973) *Advances in Chemical Psychopharmacology, Vol.* 8, M. Braudy et al. eds. (Raven Press, New York, N.Y.), at pp. 33-43. A direct and simple assay measuring physical dependence is the mouse jump test described by Saelens et al. (1971) *Arch. Int. Pharmacodyn.* 190:213. A summary of results is shown in the following table.

| Compound Evaluated | Opiate Receptor Inhibition ($IC_{50}$, nM) | | Analgesia Tail Flick $ED_{50}$ (morphine = 1) | | Antagonism (μmol/kg) | |
|---|---|---|---|---|---|---|
| | −NaCl | +NaCl | SC | Oral | Straub Tail | Tail Flick |
| N-sec-butyl normorphine (R) | 60 | 110 | 0.55 | | 16.2 | |
| N-sec-butyl normorphine (S) | 28 | 62 | 0.78 | | 7.4 | |
| N-α-methylcyclo-propylmethyl-normorphine (mixture) | 3 | 6 | 0.85 | | 4.5 | — |
| N-α-methylcyclo-propylmethyl-normorphine (S isomer) | 0.23 | — | 5.2 | 6.2 | — | >213 |
| N-α-methylcyclo-propylmethyl-normorphine (1, R isomer) | 7 | — | 0.19 | | — | >213 |
| morphine | 10 | 250 | 1 | 1 | 1 | 2 |
| nalorphine | 2 | 6 | — | — | — | — |

Diastereomer A of N-α-methylcyclopropylmethyl-normorphine (1, R isomer) had over 43 times the affinity of morphine in the opiate assay and about 122 times the affinity of N-sec-butyl-normorphine.

In the Straub tail method, the mixture of N-α-methylcyclopropylmethyl-normorphine diastereomers gave a value of 4.5 μmol/kg as an antagonist, thus being about one-fourth as potent as nalorphine (1 mmol/kg).

However, when measured by a different test, neither of the optically pure diastereomers of N-α-methylcyclopropylmethyl-normorphine was an antagonist, as judged by their inability to reverse analgesia induced by morphine in the tail flick assay up to a dose of 213 μmol/kg, although a nalorphine control was effective at 2.04 μmol/kg.

Physical dependence, a more direct measure of non-addictive properties than antagonist activity, was evaluated using the mouse jump test. Mice were injected intraperitoneally 5 times on day 1 with increasing doses of test compound ranging from 8-100 mg/kg body weight. On days 2 and 3 the mice were given 100 mg/kg 4 times. On day 4 all mice received 100 mg/kg of the antagonist naloxone in a single dose. The mice were then caged for 30 min, and a record was made of the number jumping during this time.

Morphine-treated mice, as expected, showed severe withdrawal symptoms, as evidenced by their jumping (10/10 mice). However, the N-α-methylcyclopropylmethyl-normorphine diastereomeric mixture and the isolated R and S forms of N-sec-butyl normorphine were able to reduce the number of mice jumping to about 1 in 10, as did a nalorphine control, indicating little or no addiction liability.

EXAMPLE 6

Binding Affinity

The binding affinity of N-[(1R)-1-cyclopropylethyl]-normorphine (1, R isomer) and the standard compounds [D-Ala$^2$, NMePhe$^4$, Gly$^5$-ol]-enkephalin ("DAMGO"), [D-Pen$^2$,D-Pen$^5$]-enkephalin ("DPDPE"), (5α,7α,8β)-(+)—N-methyl-N-[7-(1-pyrrolidinyl)-1-oxaspiro[4.5]dec-8-yl]-benzeneacetamide ("U69593"), and buprenorphine at opioid receptors was investigated. Binding was conducted on membranes derived from CHO cells that had been transfected with human receptors. The radioligands used were [$^3$H]DAMGO, [$^3$H]Cl-DPDPE, and [$^3$H]U69593 to bind to μ, δ, and κ receptors, respectively. A summary of the results is shown in the following table:

| Compound | $K_i$ (nM) | | |
|---|---|---|---|
| | μ | δ | κ |
| N-[(1R)-1-cyclopropylethyl]-normorphine | 0.35 ± 0.06 | 3.97 ± 0.98 | 0.43 ± 0.11 |
| DAMGO | 0.5 ± 0.05 | 300 ± 59 | 3.−05 ± 56 |
| DPDPE | 503 ± 10 | 1.7 ± 0.1 | >10,000 |
| U69593 | 1145 ± 335 | >10,000 | 1.39 ± 0.3 |
| Buprenorphine | 1.5 ± 0.08 | 4.5 ± 0.4 | 0.8 ± 0.05 |

EXAMPLE 7

Stimulation of [$^{35}$S]GTPγS Binding

Stimulation of [$^{35}$S]GTPγS binding of N-[(1R)-1-cyclopropylethyl]-normorphine (1, R isomer) and the standard compounds DAMGO DPDPE, U69593, and buprenorphine was conducted on membranes derived from CHO cells that had been transfected with human receptors. The values for percent stimulation are relative to the standard compounds DAMGO, DPDPE, and U69593 for to μ, δ, and κ receptors, respectively. A summary of the results is shown in the following table:

| Compound | μ | | δ | | κ | |
|---|---|---|---|---|---|---|
| | $EC_{50}$ (nM) | % Stim | $EC_{50}$ (nM) | % Stim | $EC_{50}$ (nM) | % Stim |
| N-[(1R)-1-cyclopropylethyl]-normorphine | >10,000 | | 39.6 ± 6.3 | 22 ± 6 | 15.2 ± 2.5 | 63 ± 1 |
| DAMGO | 13.7 ± 5.3 | 100 | >10,000 | | 4365 | 62 |
| DPDPE | >10,000 | | 1.3 ± 0.2 | 100 | 970 ± 175 | 77 |
| U69593 | >10,000 | | >10,000 | | 26.1 ± 10.7 | 100 |

-continued

| Compound | μ | | δ | | κ | |
|---|---|---|---|---|---|---|
| | EC$_{50}$ (nM) | % Stim | EC$_{50}$ (nM) | % Stim | EC$_{50}$ (nM) | % Stim |
| Buprenorphine | 2.3 ± 1.7 | 66 ± 36 | >10,000 | | >10,000 | |
| Cyclazocine | 1.2 ± 0.07 | 33 ± 18 | 2.9 ± 1.9 | 82 ± 9 | 0.80 ± 0.2 | 80 |
| (−)SKF 10,047 | >10,000 | | 9.4 ± 2.3 | 70 ± 9 | 5.38 ± 2.3 | 49 ± 13 |

EXAMPLE 8 pA$_2$ Analysis of Antagonist Activity

N-α-methylcyclopropylmethyl-normorphine (1, R isomer) was subjected to pA$_2$ analysis at the μ receptor. For this experiment, various concentrations of 1 are used in the presence of a full DAMGO dose response curve. 1 induces a parallel shift to the right of the dose response curve indicating competitive antagonist activity. With an n=6, we determined: Ke=1.43±0.16 nM, Slope=−1.04, and pA$_2$=8.84±0.06.

These experiments indicate that N-[(1R)-1-cyclopropylethyl]-normorphine (1) is a compound with high affinity at each opioid receptor site, with equal affinity at μ and κ, with slightly lower affinity at δ. Functional studies find it to be a pure antagonist in the [$^{35}$S]GTPγS assay at the m receptor, and a partial agonist at δ and κ. pA$_2$ analysis shows N-[(1R)-1-cyclopropylethyl]-normorphine (1) to be a potent competitive antagonist at μ receptors.

I claim:

1. A method for the treatment of a drug-dependent individual, comprising administering to the individual a pharmacologically active agent having the structure of formula (I)

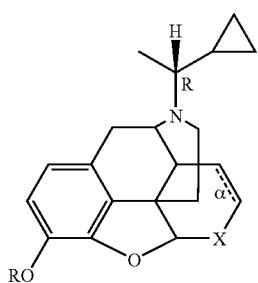

(I)

wherein:
R is H, alkyl, or acyl;
X is CH(OR') or C=O, wherein R' is H or acyl;
α is an optional double bond, with the proviso that when α is present, then X is necessarily CH(OH),
or an acid addition salt thereof, wherein the active agent is administered in an amount sufficient to act as an antagonist of a mu-opioid receptor, and wherein the drug-dependent individual is addicted to a mu-acting opiate.

2. The method of claim 1, wherein the active agent is in a stereoisomerically pure form that corresponds to that of N-α-methylcyclopropylmethyl-normorphine which melts at approximately 188° C.-189° C.

3. The method of claim 1, wherein α is present.
4. The method of claim 1, wherein α is absent.
5. The method of claim 4, wherein X is CH(OR') and R' is H.
6. The method of claim 4, wherein X is C=O.
7. The method of claim 1, wherein R is alkyl.
8. The method of claim 7, wherein R is C$_1$-C$_6$ alkyl.
9. The method of claim 8, wherein R is methyl.
10. The method of claim 1, wherein the active agent is in the form of a free base.
11. The method of claim 1, wherein the active agent is in the form of an acid addition salt.
12. The method of claim 11, wherein the acid addition salt is a salt formed with an inorganic acid.
13. The method of claim 12, wherein the acid addition salt is the hydrochloride salt.
14. The method of claim 1, wherein R is methyl, X is CH(OR'), R' is H, and α is present.
15. The method of claim 1, wherein R is methyl, X is CH(OR'), R' is H, and α is absent.
16. The method of claim 14, wherein the active agent is in the form of a hydrochloride salt.
17. The method of claim 15, wherein the active agent is in the form of a hydrochloride salt.
18. The method of claim 1, wherein the active agent is administered periodically throughout a treatment period.
19. The method of claim 18, wherein the active agent is administered at least once every 24 hours throughout the treatment period.
20. The method of claim 18, wherein the active agent is administered parenterally.
21. The method of claim 20, wherein the active agent is administered at a dose in the range of approximately 0.1 mg/kg/day to approximately 0.5 mg/kg/day.
22. The method of claim 18, wherein the active agent is orally active.
23. The method of claim 22, wherein the active agent is administered orally.
24. The method of claim 1, wherein the opiate is alfentanil, buprenorphine, butorphanol, codeine, fentanyl, heroin, hydrocodone, hydromorphone, levorphanol, meperidine, methadone, morphine, nalbuphine, oxycodone, oxymorphone, pentazocine, propoxyphene, sufentanil, or tramadol.
25. The method of claim 24, wherein the opiate is heroin.
26. The method of claim 24, wherein the opiate is hydrocodone.
27. The method of claim 24, wherein the opiate is oxycodone.

* * * * *

UNITED STATES PATENT AND TRADEMARK OFFICE
CERTIFICATE OF CORRECTION

| | | |
|---|---|---|
| PATENT NO. | : 7,629,355 B2 | Page 1 of 1 |
| APPLICATION NO. | : 10/967098 | |
| DATED | : December 8, 2009 | |
| INVENTOR(S) | : Lawson | |

It is certified that error appears in the above-identified patent and that said Letters Patent is hereby corrected as shown below:

On the cover page,

[*] Notice:   Subject to any disclaimer, the term of this patent is extended or adjusted under 35 USC 154(b) by (974) days Delete the phrase "by 974 days" and insert -- by 1,453 days --

Signed and Sealed this

Fourth Day of May, 2010

David J. Kappos
*Director of the United States Patent and Trademark Office*